United States Patent [19]

Prince et al.

[11] Patent Number: 6,020,319
[45] Date of Patent: Feb. 1, 2000

[54] NUCLEIC ACID BASED IMMUNOTHERAPY OF CHRONIC HEPATITIS B INFECTION

[75] Inventors: Alfred M. Prince, Pound Ridge, N.Y.; Betsy Brotman, Charlesville, Liberia

[73] Assignee: New York Blood Center, New York, N.Y.

[21] Appl. No.: 08/899,553

[22] Filed: Jul. 24, 1997

[51] Int. Cl.[7] .......................... A61K 48/00; A61K 35/00; C12N 15/63
[52] U.S. Cl. ........................ 514/44; 435/320.1; 424/93.2
[58] Field of Search ........................... 514/44; 435/320.1, 435/440, 455; 424/93.2

[56] References Cited

U.S. PATENT DOCUMENTS 5,643,578  7/1997  Robinson et al. .................... 424/210.1

OTHER PUBLICATIONS

Davis et al. DNA–mediated immunization to hepatitis B surface antigen: longevity of primary response and effect of boost. Vaccine, vol. 14, No. 9, pp. 910–915, Jun. 1996.
Davis, H. L. DNA–based vaccination against hepatitis B virus. Advanced Drug Delivery Reviews, vol. 21, pp. 33–47, Aug. 12, 1996.
Rabinovich et al. Vaccine Technologies: View to the Future. Science, vol. 265, pp. 1401–1404, Sep. 2, 1994.
Whalen et al. DNA–Mediated Immunization and the Energetic Immune Response to Hepatitis B Surface Antigen. Clinical Immunology and Immunotpathology, vol. 75, No. 1, pp. 1–12, 1995.
Akbar, S. M. Fazle, et al., "Placebo–controlled trial of vaccination with hepatitis B virus surface antigen in hepatitis B virus transgenic mice," *Journal of Hepatology*, vol. 26, pp. 131–137 (1997).
Ma, Z.M., et al., "Recombinant Vaccinia Virus Expressing Pre–S/S Protein of Duck Hepatitis B Virus and its Preliminary Use for Treatment of Persistent Infection," *Acta Virologica*, vol. 40, pp. 311–314 (1996).
Mancini, M., et al., "DNA–mediated immunization in a transgenic mouse model of the hepatitis B surface antigen chronic carrier state," *Proc. Natl. Acad. Sci. USA*, vol. 93, pp. 12496–12501 (Oct. 1996).
Pol, Stanislas, et al., "Efficacité d'une immunothérapie par vaccination contre le virus de l'hépatite B sur la multiplication virale B," *C. R. Acad. Sci. Paris., Sciences de la vie*, vol. 316, pp. 688–691 (1993).
Pol, Stanislas, et al., "Specific vaccine therapy in chronic hepatitis B infection ," *The Lancet*, vol. 344, p. 342 (Jul. 30, 1994).
Tartaglia, James, et al., "NYVAC: A Highly Attenuated Strain of Vaccinia Virus," *Virology*, vol. 188, pp. 217–232 (1992).

*Primary Examiner*—Bruce R. Campell
*Assistant Examiner*—Deborah J. R. Clark
*Attorney, Agent, or Firm*—Bryan Cave LLP; Maurice B. Steifel; Leo G. Lenna

[57] ABSTRACT

Method for DNA-based immunotherapy of mammalian subjects in the treatment of chronic hepatitis B infection through a series of injections of DNA transcription units encoding hepatitis B surface antigen followed by booster injections of a DNA transcription unit encoding at hepatitis B surface antigen.

18 Claims, 1 Drawing Sheet

NUCLEIC ACID BASED IMMUNOTHERAPY OF CHRONIC HEPATITIS B INFECTION

FIELD OF THE INVENTION

The present invention relates to methods for DNA-based immunotherapy of subjects infected with hepatitis B virus.

BACKGROUND OF THE INVENTION

Viral hepatitis is a general term that is reserved for infections of the liver caused by one of at least five distinct hepatitis viruses—hepatitis viruses A, B, C, D and E. Regardless of etiology, the course of acute viral hepatitis is similar and can be divided into four clinical phases: (a) the incubation period, representing time between exposure and the first days of symptoms or jaundice, (b) a prodromal or preicteric stage, (c) the icteric phase, and (c) the convalescent period. The incubation period for viral hepatitis type B ("HBV") ranges from 45 to 120 days and is affected by several factors such as the size of the inoculum and virus-host interactions. Barker, L. F. and Maynard, J. E., 1972, *Am. J Med. Sci.* 263: 27–33.

In the United States, chronic liver disease is among the ten leading causes of death in men. Nearly 50% of these deaths are in individuals less than 60 years of age. Unfortunately, the vast majority of patients with chronic hepatitis B remain asymptomatic for many years even though there may be biochemical evidence of the disease. Viral hepatitis continues to be a major public health problem. In 1993, 43,012 cases of hepatitis were reported yielding a reported incidence of about 17 cases per 100,000 people. Centers for Disease Control and Prevention. *Final* 1993 *Reports of Specified Notable Diseases.* MMWR 1994, 43: 597–603. About one third of these cases were designated as hepatitis B.

Chronic infections with HBV affect more than 200 million persons world wide. These have a high risk of development of cirrhosis and hepatocellular carcinoma. Feitelson, M., 1992, *Clin. Micro. Rev.* 5: 275–301. Termination of chronic hepatitis infection may prevent the development of these sequelae. Nucleic acid based vaccines have the potential for use in mass immunizations because of the cost and ease with which they can be combined to generate multi-valent immunogens. The high rate of vertical transmission of HBV in Asia and Africa poses a great problem—how to treat and terminate chronic HBV infection.

Attempts have been made to terminate chronic HBV infection with conventional HBV vaccine, with some success. In two reports of studies employing standard three dose immunization regimens, 3/14 and 11/42 patients became negative for HBV DNA. Pol, S. et al., 1993, *CR. Acad. Sci. III* 7: 688–691; and Pol, S. et al., 1994, *Lancet* 344, 342. Fazle Akbar, S. M., 1997, *J. Hepatology* 26: 131–137, reported that repeated monthly immunization of HBV transgenic mice with HBsAg in Freund's complete adjuvant given intraperitoneally cleared HBsAg in 25/32 mice. This strategy cannot be directly applied to man due to the toxicity of Freund's complete adjuvant.

Mancini, et al reported clearance of circulating HBsAg, and liver HBV RNA from transgenic mice encoding the HBV genome with the core gene deleted, following immunization with a single injection of a plasmid encoding S and Pre-S2 determinants of HBV. Mancini, M., 1996, *Proc. Natl. Acad. Sci.* USA 93: 12496–12501. Duck hepatitis B virus recombinant vaccinia virus has also been used in an attempt to terminate chronic duck hepatitis B infection. Ma, Z. M., Kong, Y. Y., Wang, Y., Wen, Y. M., 1996, *Acta Virologica* 40: 311–314. A temporary drop in surface antigen titer, but no permanent resolution, was observed.

Immunotherapeutic treatment of chronically infected subjects following administration of DNA-based immunization to induce termination of HBV DNA replication with HBsAg determinants have not been carried out or evaluated in chronically infected mammals heretofore.

SUMMARY OF THE INVENTION

The present invention relates to methods for DNA-based immunotherapy of mammalian subjects in the treatment of chronic hepatitis B infection. More specifically, the DNA based immunization comprises injection of DNA transcription units encoding at least one hepatitis B surface antigen (HBsAg) determinants, followed by booster injections of DNA transcription units encoding at least one HBsAg determinant.

The method of the invention comprises administering to a chronically infected subject a first DNA transcription unit which comprises DNA encoding at least one hepatitis B surface antigen (HBsAg) and a leader sequence for the secretion of translated protein. The uptake of the DNA transcription unit by host cells results in the expression and secretion of the hepatitis B antigen or antigens, thereby eliciting an immune response. The elicited immune response provides immunotherapeutic treatment of chronic hepatitis B infection. Subsequent to administration of the first transcription unit, a second DNA transcription unit is administered, comprising DNA encoding at least one HBsAg. The uptake of the second DNA transcription unit by host cells results in the expression of the hepatitis B antigen or antigens, thereby eliciting a second immune response. Subsequent to administration of the second transcription unit, a third DNA transcription unit is administered, comprising DNA encoding at least one HBsAg. The third DNA transcription unit is contained in an attenuated vaccine virus capable of infecting mammalian cells, but not replicating in them. The third transcription unit is comprised of at least one expression cassette encoding at least one hepatitis B surface antigen. The uptake of the third DNA transcription unit by host cells results in the expression of the hepatitis B antigen or antigens, thereby eliciting an third booster immune response.

DETAILED DESCRIPTION OF THE INVENTION

Figure 1:
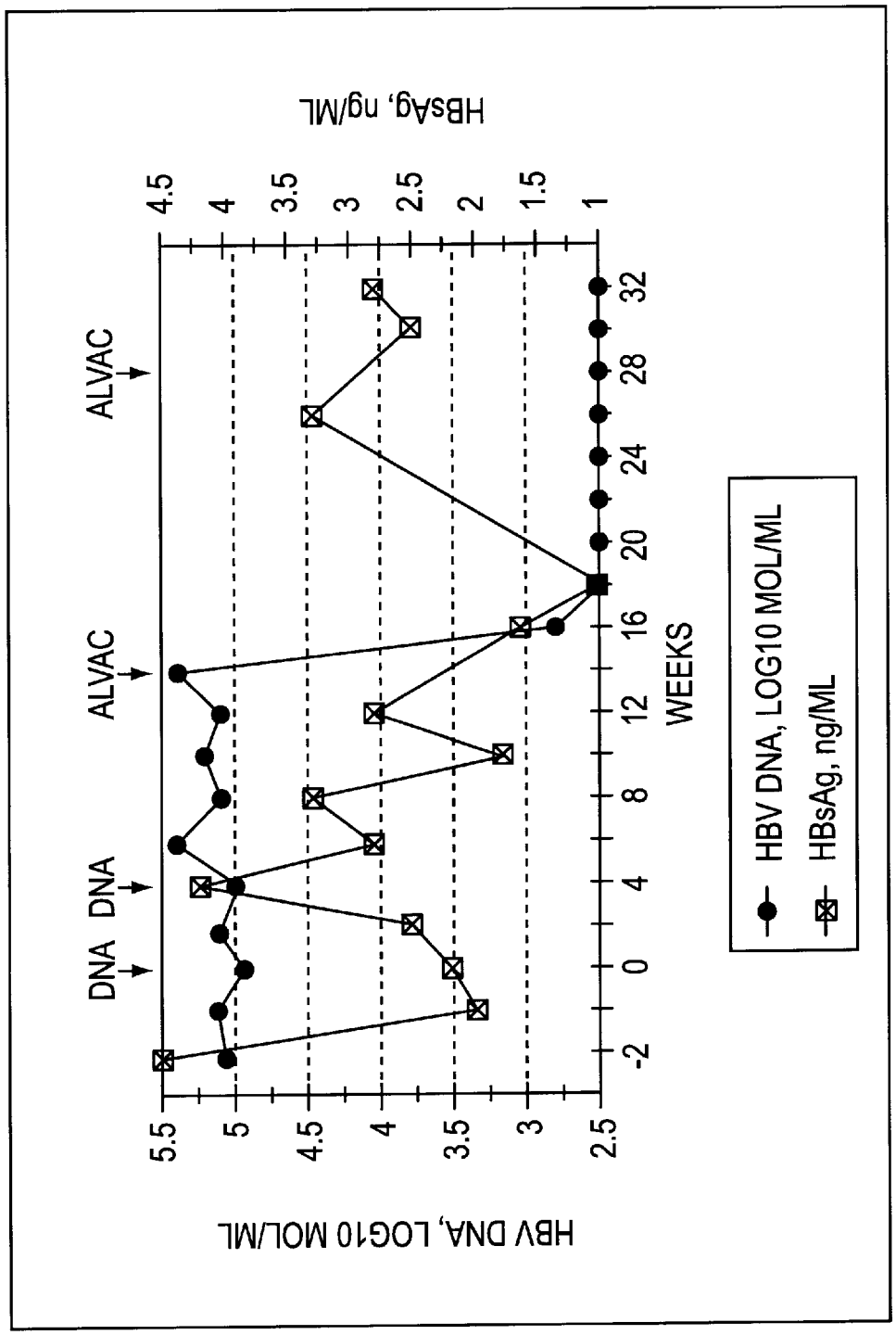
FIG. 1 represents the results of immunization and booster challenge of a chimpanzee chronically infected with HBV.

In accordance with the present invention, mammalian subjects chronically infected with HBV are immunized against hepatitis B antigen or antigens, thereby eliciting an immune response which provides immunotherapeutic treatment of chronic hepatitis infection through the termination of HBV viral DNA replication. The methods of the invention induce protective immunotherapeutic treatment in chronically infected mammals, particularly humans, ranging in age from infant to adult.

Direct gene transfer may be carried out using viral vectors or recombinant plasmid DNA carrying cloned genes to be expressed in situ. The use of pure plasmid DNA offers advantages over the viral vectors for the purpose of immunization, e.g., greater ease and speed of production, easier quality control, non-integration of the DNA, lack of immunogenicity of the vector itself, the ease and lower cost of production for use in developing countries, and the heat stability of DNA which can be stored in a lyophilized form or at 4° C.

The term "immunizing" used herein refers to the generation of an immune response which provides ameliorative treatment (partially or totally) for chronic infection.

The term "DNA-based immunization" used herein refers to the induction of an immune response to a protein antigen expressed in vivo subsequent to the administration of plasmid or vector DNA encoding the polypeptide sequence. The resulting in situ production of the protein may involve biosynthetic processing and post-translational modifications. This method of immunization differs from the use of classical vaccines, which are composed of the antigen in the form of whole pathogen, a killed virus or bacteria, an attenuated virus or bacteria, or a subunit component (e.g. purified or recombinant proteins or synthetic peptides).

The term "chronically infected" used herein is defined as those individuals remaining positive for the presence of both HBV DNA, as measured through standard PCR assay methods (see materials and methods below), and the presence of hepatitis B surface antigen (HBsAg), as measured through standard antibody test screening, for at least one year following infection with the virus.

The term "protective immunotherapeutic treatment" used herein is defined as the termination of HBV DNA production following DNA-based immunization with HBsAg determinants.

Ultra structural examination of sera from hepatitis B patients shows three distinct morphological forms: the complete hepatitis B virion (HBV), a 42-nm double-shelled particle that consists of an envelope composed of hepatitis B surface antigen (HBsAg), an inner core hepatitis B core antigen (HBcAg) closely associated with the nucleocapsid containing its own distinct antigen and the hepatitis Be antigen (HBeAg).

HBsAg is encoded by a single gene with a large open reading frame containing three start codons which divide the gene into S, pre-S1 and pre-S2. The three different sized polypeptides which can be produced are known as the small (S), middle (M, pre-S2+S) and large (L, pre-S1+pre-S2+S) proteins. The envelope of the infectious particle of HBV contains all three forms. Davis, H. L., et al., 1994 *Vaccine* 12: 1503–1509.

The immunotherapeutic method of the invention involves: Injection of an immunotherapeutically effective amount of a first secretor plasmid containing a DNA transcription unit encoding HBsAg S protein, wherein the plasmid is capable of replicating in a mammalian cell and contains a transcription unit encoding a translated leader sequence which will provide the translated HBsAg S protein with the ability to be secreted from the cell following protein production. The gene encoding the HBsAg S protein is inserted in the transcription unit such that it is in frame with the promoter and leader sequences contained in the plasmid and such that the HBsAg S open reading frame of the protein will be generated in frame.

The first secretor plasmid is administered at day 0 by injecting intramuscularly.

An immunotherapeutically effective amount of a second, non-secretor plasmid is subsequently injected, the non-secretor plasmid containing a DNA transcription unit encoding HBsAg S protein wherein the plasmid is capable of replicating in a mammalian cell, and wherein the plasmid does not contain any transcription unit encoding a leader sequence required for secretion of translated protein. The gene encoding the HBsAg S protein is inserted in the transcription unit such that it is in frame with the promoter sequence contained in the plasmid such that the HBsAg S open reading frame of the protein will be generated in frame.

The second non-secretor plasmid is administered 2–6 weeks following day 0 by injecting intramuscularly. A particularly preferred time for injection of the second non-secretor plasmid is at week 4.

Following administration of the first and second plasmid transcription units, an immunotherapeutically effective amount of a booster injection of an attenuated vaccine virus is administered. The attenuated virus is capable of infecting mammalian cells, but not replicating in them, and it contains at least one expression cassette, encoding at least one of the following hepatitis surface antigens of HBV: the L form, comprised of HBsAg(S), pre-S1 and Pre-S2; and the M form, comprised of HBsAg(S) and Pre-S2.

Booster injections of the non-replicating vaccine may be given both intramuscularly and intravenously, e.g., at weeks 13–17 and weeks 26–30. Particularly preferred times for booster injections of the non-replicating vaccine are given at 15 weeks and 28 weeks.

Any appropriate physiologically compatible medium is suitable for introducing the plasmid or booster injections into an individual. A particularly preferred medium is phosphate buffered saline (PBS).

A suitable immunization dosage for inducing the immunotherapeutic treatment of chronically infected subjects is as follows: On a dose-per-kilogram basis, a subject receives intramuscular injections of 0.004 to 0.5 mg per kilogram body weight per injection for both the first secretor and second non-secretor plasmid DNA encoding the HBsAg S protein. Each injection is given in a volume of 1–3 milliliters. A particularly preferred volume is 2.0 milliliters. The non-replicating viral booster vaccine is given at a dose of $10^6$–$10^8$ PFU per kilogram body weight. Each intramuscular or intravenous booster injection is administered in a volume of 0.25–1 milliliter. A particularly preferred volume is 0.50 milliliter.

For intramuscular injection of plasmid DNA transcription unit and booster injections, each administration is administered at 1–20 different sites. A particularly preferred number of sites for intramuscular injection administration is different 4 sites.

EXAMPLE

This Example illustrates the treatment of a mammal chronically infected with hepatitis B virus, i.e. in the chronic carrier state. Immunization with HBsAg-encoding plasmids, followed by boosting with a canary pox vaccine encoding HBsAg, resulted in disappearance of detectable HBV DNA beginning one week after the canary pox booster, and persisting for the duration of follow up.

Plasmid Constructs

Plasmid pJW-So, which encodes and secretes the product of the S gene of HBV, is used for the first DNA based immunization. The pJW-So plasmid is based on pJW4303, which contains genes coding for β-lactamase, SV40 origin of replication, CMV iA promoter and the bovine growth hormone TPA leader sequence. The S gene of HBV strain ayw was inserted into the polylinker NheI/Bgl II site using a PCR sequence with an upstream primer containing an NheI site and hybridized to the second 5' amino acid codon of the S gene. A primer was used for the 3' end of the S gene which contained a Bgl II site. The sequence coding for 225 amino acids of the S gene was inserted by the above strategy resulting in the 5' end in frame with the TPA leader at the NheI site.

Plasmid pIII-So, which encodes HBsAg, but does not secrete HBsAg, is used for the second DNA based immunization at 4 weeks. This construct is based on the pCDNA3 plasmid (Invitrogen Corp., San Diego, Calif.) which contains genes coding for B-lactamase, SV40 origin of replication, CMV major intermediate early promoter/enhancer region and the bovine growth hormone polyadenylation signal. The plasmid lacks any leader sequence for secretion. The S gene of HBV strain ayw was inserted into the polylinker HindIIII/Bgl II site following the procedure as described above for the pJW-So plasmid using a PCR sequence with an upstream primer containing a HindIII site and hybridized to the second 5' amino acid codon of the S gene. A primer was used for the 3' end of the S gene which contained a Bgl II site. The sequence coding for 225 amino acids of the S gene was inserted by this strategy resulting in the 5' end in frame at the HindIII site.

The plasmids were purified by double banding in CsCl-ethidium bromide gradients.

Canary Pox Construct

The canary pox construct: ALVAC HBV L;M (vCP 157) utilizes as a vector the ALVAC vaccine strain of canary pox. Virogenetics Corp., Troy N.Y.; and Tartaglia, J. et al., 1992, *Virology* 188: 217–232. ALVAC HBV L;M contains two expression cassettes, which encode two different forms of the surface antigen of the ayw strain of HBV: the L form, comprised of HBsAg(S), pre-S1 and Pre-S2; and the M form, comprised of HBsAg(S) and Pre-S2.

Chronically Infected Chimpanzee

Chimp 292, Mrs. Thatcher, was born in 1981 and became chronically infected with HBV following an experiment in which HBV was inoculated in 1985. The animal remained HBsAg positive for the 12 years since infection. After the acute phase of infection, the liver histology, PCR HBV DNA assays and HBsAg protein assays were characteristic of chronic persisting hepatitis until the end of follow up.

Immunization

Chronically infected Chimp 292 was injected with 2 ml containing 2.0 mg of pJW-So plasmid (secretor) DNA in Phosphate Buffered Saline (PBS) intramuscularly in the deltoid and quadriceps muscles at 4 different sites at week 0.

On week 4, Chimp 292 was injected with 2 ml containing 2.0 mg pIII-So plasmid (non-secretor) DNA in PBS intramuscularly at 4 different sites as described for the pJW-So immunization.

On week 15, Chimp 292 was boosted with ALVAC HBV L;M. $4 \times 10^8$ PFU in 0.50 ml of PBS intramuscularly (bilaterally) at 4 different sites and $4 \times 10^8$ PFU in 0.50 ml of PBS intravenously. This booster procedure was repeated on week 28.

Skin Tests

On weeks 17 and 30 skin tests are performed by intradermal injection of 10, 1, and 0.1 ug of purified inactivated HBsAg. (Wuhan Institute of Biological Products, Wuhan, China.) This antigen is prepared from infected plasma by ammonium sulfate precipitation, CsCl banding, and pepsin digestion. The antigen is inactivated with formalin, but is not alum adjuvanted.

PCR Assay for HBV DNA

DNA was isolated from serum using QiaAmp kits (Diagen, Hilden, Germany) according to manufacturer's instructions.

Quantitative HBV DNA assays were carried out using the AmpliSensor assay system, in accordance with the manufacturer's instructions (Biotronics, Lowell, Mass.). The AmpliSensor system monitors the amplification of the PCR reaction via a fluorescence resonance energy transfer (FRET). Initially a sequence from the HBsAg gene was produced in an asymmetric manner generating a 241 nucleotide single stranded DNA. This was then reamplified in a semi-nested manner in the presence of a fluorescent primer duplex, yielding a 66 bp amplicon which is quantitated using the Amplisensor Minilyzer (Biotronics). A plasmid encoding the HBsAg gene was provided by Biotronics for use as a standard for quantitation. Serial dilutions of this plasmid were run in duplicate in every run. The Accugene system is based on serial fluorescence measurements carried out between the 22nd and 41st cycle. Thus the microplates were sealed throughout the cycling and reading procedure. This contributes greatly to the control of contamination. PCR set up was carried out in a laminar flow hood in a dedicated room from which plasmids and amplicons are excluded.

Quantitation of HBsAg

Quantitative determinations of HBsAg were carried out by the procedure of Hollinger et al, using the WHO International HBsAg standard as a potency standard. Hollinger, F. B., Troisi, C. L., Pepe, P. E., 1986, *J Infect. Dis.* 153: 156–159.

Assays for HBeAg and anti-HBE

HBeAg and anti-HBe were detected with kits provided by Abbott Laboratories (North Chicago, Ill.).

Results

FIG. 1 summarizes the results of this study. HBV DNA levels fluctuated between 5.0 and 5.4 $\log_{10}$HBV DNA molecules/ml until week 14, just before the ALVAC booster. One week after the booster the HBV DNA level fell to 2.8 $\log_{10}$HBV DNA molecules/ml. Thereafter HBV became non-detectable at the sensitivity of the assay (<2.5 $\log_{10}$ DNA molecules/ml) for the 22 week duration of follow up.

The HBsAg content dropped only modestly after the ALVAC booster, and then returned to normal levels. No abnormalities were seen in transaminase (ALT, AST) levels (data not shown).

Prior to treatment the animal was positive for both HBeAg and anti-HBe. Shortly after ALVAC treatment HBeAg became negative while anti-HBe remained positive, however on weeks 28 and 30 HBeAg returned and anti-HBe disappeared.

The skin tests revealed no induration at any concentration when read at 24 and 48 hours, i.e. no sensitivity was observed.

The present invention thus provides for a treatment of chronic hepatitis B viral infection through the long lasting inhibition of HBV replication resulting from DNA based immunization with HBsAg determinants followed by a booster. This therapeutic immunization provides for the treatment and control of replication of HBV in patients with chronic hepatitis B infection. Control of virus replication in this manner may prevent the chronic sequelae of the chronic carrier state from occurring.

The present invention is not to be limited in scope by the specific embodiments or models described herein. Indeed, various modifications of the invention in addition to those described herein will become apparent to those skilled in the art from the foregoing description. Such modifications are intended to fall within the scope of the appended claims.

We claim:

1. A method for DNA-based immunotherapy of mammalian subjects chronically infected with hepatitis B virus, comprising:

(a) administering an immunotherapeutically effective amount of a first DNA transcription unit comprising DNA encoding at least one hepatitis B surface antigen and a leader sequence for the secretion of translated protein, to a subject, wherein the uptake of the DNA transcription unit by host cells results in the expression and secretion of the hepatitis B surface antigen and elicits an immune response;

(b) subsequent to administration of the first transcription unit, administering an immunotherapeutically effective amount of a second DNA transcription unit, comprising DNA encoding at least one hepatitis B surface antigen, to said subject, wherein the uptake of the second DNA transcription unit by host cells results in the expression of the hepatitis B antigen and elicits a second immune response;

(c) subsequent to administration of the second transcription unit, administering an immunotherapeutically effective amount of a third DNA transcription unit, comprising at least one DNA expression cassette encoding at least one hepatitis B surface antigen contained in an attenuated ALVAC vaccine virus, to said subject, wherein the uptake of the third DNA transcription unit by host cells results in the expression of the hepatitis B antigen, thereby eliciting a booster immune response;

wherein the DNA replication of hepatitis B virus is inhibited in said subject.

2. The method according to claim 1, wherein the first and second DNA transcription units are contained on DNA plasmids.

3. The method according to claim 2, wherein the administrations of each of the plasmids containing the first and second DNA transcription units comprises a dose of 0.004–0.50 milligrams of plasmid DNA per kilogram of body weight.

4. The method according to claim 1, wherein the first and second DNA transcription units are comprised of a gene encoding hepatitis B surface antigen S protein.

5. The method according to claim 4, wherein the gene encoding hepatitis B surface antigenS protein is derived from the hepatitis B ayw strain.

6. The method according to claim 1, wherein the third DNA transcription unit is comprised of two expression cassettes, containing genes respectively encoding the L and M forms of hepatitis B surface antigen.

7. The method according to claim 6, wherein the genes encoding the L and M forms of hepatitis B surface antigen are derived from the hepatitis B ayw strain.

8. The method according to claim 1, wherein the first and second DNA transcription units are injected intramuscularly at 1–20 sites.

9. The method according to claim 1, wherein the third DNA transcription unit contained in the attenuated vaccine virus is administered in a dose of about $10^6$–$10^8$ PFU per kilogram of body weight.

10. The method according to claim 1, wherein the second DNA transcription unit is administered 2–6 weeks following the administration of the first DNA transcription unit.

11. The method according to claim 1, wherein the second DNA transcription unit is administered 4 weeks after administration of the first DNA transcription unit.

12. The method according to claim 1, wherein the third DNA transcription unit is administered at weeks 13–17 and weeks 26–30.

13. The method according to claim 1, wherein the third DNA transcription unit is administered at week 15 and week 28.

14. The method according to claim 1, wherein the first and second DNA transcription units are administered intramuscularly in a volume of 1–3 milliliters.

15. The method according to claim 14, wherein the intramuscular injections are administered in a volume of about 2.0 milliliters.

16. The method according to claim 1, wherein of the third DNA transcription unit is administered intramuscularly and intravenously.

17. The method according to claim 16, wherein of the third DNA transcription unit is administered in a volume of about 0.25–1 milliliter.

18. The method according to claim 17, wherein of the third DNA transcription unit is administered in a volume 0.50 milliliter.

* * * * *

UNITED STATES PATENT AND TRADEMARK OFFICE
CERTIFICATE OF CORRECTION

PATENT NO. : 6,020,319
DATED : February 1, 2000
INVENTOR(S) : Alfred M. PRINCE; Betsy BROTMAN It is certified that error appears in the above-identified patent and that said Letters Patent is hereby corrected as shown below:

In claims 16, column 8, line 32, after "wherein", delete "of".

In claims 17, column 8, line 35, after "wherein", delete "of".

In claims 18, column 8, line 38, after "wherein", delete "of".

Signed and Sealed this

Second Day of January, 2001

Attest:

Attesting Officer

Q. TODD DICKINSON
Commissioner of Patents and Trademarks